United States Patent
Hein

(10) Patent No.: US 9,921,145 B2
(45) Date of Patent: Mar. 20, 2018

(54) METHOD FOR DETERMINING DEGRADATION OF THERMOPLASTICS

(71) Applicant: SABIC Global Technologies B.V., Bergen op Zoom (NL)

(72) Inventor: Christopher Luke Hein, Evansville, IN (US)

(73) Assignee: SABIC GLOBAL TECHNOLOGIES B.V., Bergen op Zoom (NL)

( * ) Notice: Subject to any disclaimer, the term of this patent is extended or adjusted under 35 U.S.C. 154(b) by 0 days.

(21) Appl. No.: 15/343,300

(22) Filed: Nov. 4, 2016

(65) Prior Publication Data
US 2017/0052108 A1  Feb. 23, 2017

Related U.S. Application Data

(63) Continuation of application No. 14/159,579, filed on Jan. 21, 2014, now Pat. No. 9,557,218.

(60) Provisional application No. 61/755,637, filed on Jan. 23, 2013.

(51) Int. Cl.
| | |
|---|---|
| *G01N 17/00* | (2006.01) |
| *G01J 3/42* | (2006.01) |
| *B01J 19/12* | (2006.01) |
| *G01N 21/25* | (2006.01) |
| *G01N 33/44* | (2006.01) |

(52) U.S. Cl.
CPC .......... *G01N 17/004* (2013.01); *B01J 19/123* (2013.01); *G01J 3/42* (2013.01); *G01N 21/25* (2013.01); *G01N 21/251* (2013.01); *G01N 21/255* (2013.01); *G01N 33/442* (2013.01)

(58) Field of Classification Search
None
See application file for complete search history.

(56) References Cited

U.S. PATENT DOCUMENTS

| | | | |
|---|---|---|---|
| 2,500,229 | A | 3/1950 | Arnold et al. |
| 3,693,020 | A | 9/1972 | Ackerman, Jr. |
| 4,493,915 | A | 1/1985 | Lohmeijer |
| 4,770,542 | A | 9/1988 | Takagi |

(Continued)

FOREIGN PATENT DOCUMENTS

| | | |
|---|---|---|
| DE | 2133797 | 1/1973 |
| FR | 2430609 | 2/1980 |

(Continued)

OTHER PUBLICATIONS http://web.archive.org/web/20120916114639/http://en.wikipedia.org/wiki/Polymer_degradation, Sep. 16, 2012.

(Continued)

*Primary Examiner* — Shawn Decenzo
(74) *Attorney, Agent, or Firm* — Baker & Hostetler LLP

(57) ABSTRACT

A method of determining degradation of a thermoplastic when exposed to light and heat includes illuminating the thermoplastic with a desired wavelength of light at a desired irradiance while maintaining the ambient air surrounding the thermoplastic at a desired temperature. The method is useful to measure the discoloration rate of transparent, translucent and opaque thermoplastics such as polycarbonates, the discoloration rate being determined by transmission or reflectance spectra of transmitted or reflected white light through or from the thermoplastic.

18 Claims, 3 Drawing Sheets

(56) References Cited

U.S. PATENT DOCUMENTS

| | | | |
|---|---|---|---|
| 4,848,090 | A | 7/1989 | Peters |
| 5,154,889 | A | 10/1992 | Muraishi |
| 5,541,239 | A | 7/1996 | Heywood, Jr. |
| 6,576,911 | B1 | 6/2003 | Potyrailo et al. |
| 2003/0234286 | A1 | 12/2003 | Labrec et al. |
| 2004/0211900 | A1 | 10/2004 | Johnson |
| 2006/0027035 | A1* | 2/2006 | Ketola ............... G01N 17/004 73/865.6 |
| 2006/0068316 | A1 | 3/2006 | Engle et al. |
| 2010/0215942 | A1* | 8/2010 | Casati ............... B32B 5/18 428/304.4 |
| 2011/0260638 | A1* | 10/2011 | Gotay ............... H01J 5/54 315/291 |
| 2012/0271445 | A1 | 10/2012 | Li et al. |

FOREIGN PATENT DOCUMENTS

| | | |
|---|---|---|
| GB | 2060180 | 4/1981 |
| JP | 2006308308 | 11/2006 |
| JP | 2009250699 | 10/2009 |
| WO | 199936763 | 7/1999 |

OTHER PUBLICATIONS http://web.archive.org/web/20130121014603/http://en.wikipedia.org/wiki/Sunlight, Jan. 21, 2013.

Altria, et al. "The Application of Experimental Design to the Robustness Testing of a Method for the Determination of Drug-Related Impurities by Capillary Electrophoresis," Chromatographia, 1994, 39(5/6), 306-310.

Liu et al., "Solid-Phase Photocatalytic Degradation of Polyethylene-Goethite Composite Film Under UV-Light Irradiation", Journal of Hazardous Materials, Dec. 30, 2009, 172(2-3), 1424-1429.

Reiling, Characteristics of Mercury Vapor-Metallic Lodide Arc Lamps, Journal of the Optical Society of America, Apr. 1964, pp. 532-540, vol. 54, No. 4.

International Patent Application No. PCT/US2014/012693: International Search Report and Written Opinion dated Apr. 16, 2014, 16 pages.

International Patent Application No. PCT/US2014/012701: International Search Report and Written Opinion dated Mar. 27, 2014, 10 pages.

\* cited by examiner

METHOD FOR DETERMINING DEGRADATION OF THERMOPLASTICS

CROSS REFERENCE TO RELATED APPLICATION

This application is a continuation of, and claims priority to U.S. patent application Ser. No. 14/159,579, which is based upon and claims priority to U.S. Provisional Application No. 61/755,637, filed Jan. 23, 2013, both of which are hereby incorporated by reference.

FIELD OF THE INVENTION

This invention concerns a method for determining the degradation of thermoplastics, such as the rate of discoloration of opaque, translucent and transparent polycarbonates, when subjected to heat and light.

BACKGROUND

Thermoplastics comprise a large family of polymers, most of which have a high molecular weight. Intermolecular forces are responsible for the association of the molecular chains, which allows thermoplastics to be heated and remolded. Thermoplastics become pliant and moldable at a temperature above their glass transition temperature but below their melting point, and the intermolecular forces reform after molding and upon cooling of the thermoplastic, resulting in the molded product having substantially the same physical properties as the material prior to molding.

Polycarbonates fall within the thermoplastic family and contain carbonate groups —O—(C=O)—O—. Polycarbonates find widespread use throughout industry due to their excellent strength and impact resistance. Additionally, polycarbonates may be readily machined, cold-formed, extruded, thermoformed and thermomolded.

Exposure of thermoplastics to light is known to induce changes to the polymer. In particular, the exposure of opaque, translucent and transparent polycarbonates to blue LED (light emitting diode) light is of interest for the manufacture of efficient illumination devices such as lamps and other types of lighting apparatuses. Transparent is defined as a light transmittance of at least 80% when tested in the form of a 3.2 mm thick test sample according to ASTM D1003-00 (2000) (hereby incorporated by reference). Translucent is defined as a light transmittance greater than or equal to 40% when tested in the form of a 2.5 mm thick test sample according to ASTM D1003-00 (2000). Opaque is defined as a light transmittance of 10% or greater when tested in the form of a 3.2 mm thick test sample according to ASTM D1003-00 (2000). The testing according to ASTM D1003-00 (2000) uses procedure A and CIE illuminant C and 2 degree observer on a CE7000A using an integrating sphere with 8°/diffuse geometry, specular component included, UV included, large lens, and large area view, with percentage transmittance value reported as Y (luminous transmittance) taken from the CIE 1931 tristimulus values XYZ.

Blue LED light having a peak intensity from about 400 nm to about 500 nm and an irradiance from about 3,500 $W/m^2$ to about 120,000 $W/m^2$ is of particular interest. Similarly, white LED light having a peak intensity from about 400 nm to about 500 nm and an irradiance less than 120,000 $W/m^2$ is also of interest.

Opaque and translucent polycarbonate may be formed, for example, using titanium dioxide compounded with the polycarbonate formulation. Furthermore, remote phosphors, also known as "luminescent conversion materials", can be compounded into the polycarbonate. Examples of luminescent conversion materials include yttrium aluminum garnet (YAG) doped with rare earth elements, terbium aluminum garnet doped with rare earth elements, silicate (BOSE) doped with rare earth elements; nitrido silicates doped with rare earth elements; nitride orthosilicate doped with rare earth elements, and oxonitridoaluminosilicates doped with rare earth elements.

Translucent polycarbonates are formed using scattering agents such as light diffusers. The light diffusers often take the form of light diffusing particles and are used in the manufacture of articles that have good luminance. Such articles provide a high level of transmission of incident light (such as natural light through a window or skylight, or artificial light) with a minimum light loss by reflectance or scattering, where it is not desirable to either see the light source or other objects on the other side of the article.

An article e.g., a sheet having a high degree of hiding power (i.e., luminance) allows a significant amount of light through, but is sufficiently diffusive so that a light source or image is not discernible through the panel. Light diffusers can be (meth)acrylic-based and include poly(alkyl acrylate)s and poly(alkyl methacrylate)s. Examples include poly(alkylmethacrylates), specifically poly(methyl methacrylate) (PMMA). Poly(tetrafluoroethylene) (PTFE) can also be used. Light diffusers also include silicones such as poly (alkylsilsesquioxanes), for example poly(alkylsilsesquioxane)s such as the poly(methylsilsesquioxane) available under the trade name TOSPEARL® from Momentive Performance Materials Inc. The alkyl groups in the poly(alkyl acrylate)s, poly(alkylmethacrylate)s and poly(alkylsilsesquioxane)s can contain one to about twelve carbon atoms. Light diffusers can also be cross-linked. For example, PMMA can be crosslinked with another copolymer such as polystyrene or ethylene glycol dimethacrylate. In a specific embodiment, the polycarbonate composition comprises a light diffusing crosslinkedpoly(methyl methacrylate), poly (tetrafluoroethylene), poly(methylsilsesquioxane), or a combination comprising at least one of the foregoing.

Light diffusers also include certain inorganic materials, such as materials containing antimony, titanium, barium, and zinc, for example the oxides or sulfides of antimony, titanium, barium and zinc, or a combination containing at least one of the forgoing. As the diffusing effect is dependent on the interfacial area between polymer matrix and the light diffuser, in particular the light diffusing particles, the particle size of the diffusers can be less than or equal to 10 micrometers (μm). For example, the particle size of poly(alkylsilsesquioxane)s such as poly(methylsilsesquioxane) can be 1.6 μm to 2.0 μm, and the particle size of crosslinked PMMA can be 3 μm to 6 μm. Light diffusing particles can be present in the polycarbonate composition in an amount of 0 to 1.5%, specifically 0.001 to 1.5%, more specifically 0.2% to about 0.8% by weight based on the total weight of the composition. For example, poly(alkylsilsesquioxane)s can be present in an amount of 0 to 1.5 wt. % based on the total weight of the composition, and crosslinked PMMA can be present in an amount of 0 to 1.5 wt. % based on the total weight of the composition.

While the physical characteristics of strength and impact resistance make polycarbonates desirable for use as covers and lenses in LED lighting, exposure of the polycarbonate to the blue light of the LEDs (as well as the light of organic LEDs) causes degradation of the polycarbonate in the form of discoloration. For example, transparent polycarbonate is known to turn yellow, even darkening to brown, with exposure to blue light. This degradation of the transparent polycarbonate is unacceptable because the yellowed polycarbonate absorbs the light thereby reducing the efficiency of the lamp. Furthermore, the yellowing changes the color of the light emanating from the lamp, which is also unacceptable. In addition, the transparent polycarbonate is also subject to elevated temperatures when it comprises part of an LED lamp. The elevated temperatures likely play a role in the yellowing of the transparent polycarbonate.

There is clearly a need for a method to determine the degradation of thermoplastic formulations, in particular, the rate of discoloration of opaque, translucent and transparent polycarbonate formulations when exposed to light, and thereby be able to evaluate and compare the different formulations as to their suitability for use in LED lamps. It is desirable that the method provide an accelerated test of the thermoplastic which is not too slow so as to be impractical, and not too fast, so as to destroy the samples before meaningful comparisons can be made between formulations.

SUMMARY

The invention concerns a method for determining degradation of a thermoplastic, such as transparent polycarbonate, and includes at least the following embodiments.

Example Embodiment 1

A method for determining degradation of a thermoplastic, the method comprising:
  illuminating the thermoplastic with light having a peak intensity centered at a wavelength from about 400 nm to about 500 nm and an irradiance from about 3,500 $W/m^2$ to about 120,000 $W/m^2$ for a period of time;
  maintaining ambient air surrounding the thermoplastic at a temperature from about 23° C. to about 175° C. during the period of time;
  repeating the illuminating and maintaining steps for a plurality of successive periods of time.

Example Embodiment 2

The method of embodiment 1, further comprising evaluating the degradation of the thermoplastic after each successive period of time.

Example Embodiment 3

The method of embodiment 2 further comprising:
  repeating the illuminating, maintaining and evaluating steps for a plurality of successive time periods for a plurality of different thermoplastic formulations; and
  comparing the degradation of the plurality of different thermoplastic formulations with one another.

Example Embodiment 4

The method of embodiment 1, wherein the degradation comprises a discoloration rate of the thermoplastic.

Example Embodiment 5

The method of embodiment 2, wherein evaluating the degradation comprises visually inspecting the thermoplastic.

Example Embodiment 6

The method of embodiment 2, wherein evaluating the degradation comprises measuring a degree of discoloration of the thermoplastic.

Example Embodiment 7

The method of embodiment 1, wherein the irradiance is from about 70,000 $W/m^2$ to about 110,000 $W/m^2$.

Example Embodiment 8

The method of embodiment 1, wherein the irradiance is about 100,000 $W/m^2$.

Example Embodiment 9

The method of embodiment 1, wherein the peak intensity of the light is centered at a wavelength from about 410 nm to about 480 nm.

Example Embodiment 10

The method of embodiment 1, wherein the peak intensity of the light is centered at a wavelength of about 459 nm.

Example Embodiment 11

The method of embodiment 1, wherein the ambient air is maintained at a temperature from about 90° C. to about 130° C.

Example Embodiment 12

The method of embodiment 1, wherein the ambient air is maintained at a temperature of about 120° C.

Example Embodiment 13

The method of embodiment 1, further comprising cooling the thermoplastic.

Example Embodiment 14

The method of embodiment 6, wherein measuring the degree of discoloration of the thermoplastic comprises:
  illuminating the thermoplastic with white light, a portion of the white light being transmitted through the thermoplastic; and
  generating a transmission spectrum from the portion of the white light transmitted through the thermoplastic.

Example Embodiment 15

The method of embodiment 6, wherein measuring the degree of discoloration of the thermoplastic comprises:
  illuminating the thermoplastic with white light, a portion of the white light being reflected from the thermoplastic; and
  generating a reflectance spectrum of the portion of the white light reflected from the thermoplastic.

Example Embodiment 16

The method of embodiment 6, further including comparing the degree of discoloration measured after each of the successive periods of time with one another.

Example Embodiment 17

The method of embodiment 1, wherein each of the successive periods of time is equal in duration.

Example Embodiment 18

The method of embodiment 17, wherein each of the successive periods of time is about 100 hours in duration.

Example Embodiment 19

The method of embodiment 1, wherein said thermoplastic is a polycarbonate.

Example Embodiment 20

The method of embodiment 1, wherein the thermoplastic may be transparent, translucent or opaque thermoplastics.

Example Embodiment 21

A method for determining a discoloration rate of a polycarbonate, the method comprising:
 illuminating the polycarbonate with light having a peak intensity centered at a wavelength from about 400 nm to about 500 nm and an irradiance from about 3,500 $W/m^2$ to about 120,000 $W/m^2$ for a first period of time;
 maintaining ambient air surrounding the polycarbonate at a temperature from about 23° C. to about 175° C. during the first period of time.

Example 22

The method of embodiment 21, further comprising evaluating a degree of discoloration of the polycarbonate after the first period of time has elapsed.

Example Embodiment 23

The method of embodiment 21, further comprising:
 repeating said illuminating, maintaining and measuring steps for a plurality of different polycarbonate formulations; and
 comparing the discoloration of said plurality of different polycarbonate formulations with one another.

Example Embodiment 24

The method of embodiment 21, wherein the irradiance is from about 70,000 $W/m^2$ to about 110,000 $W/m^2$.

Example Embodiment 25

The method of embodiment 21, wherein the irradiance is about 100,000 $W/m^2$.

Example Embodiment 26

The method of embodiment 21, wherein the peak intensity of the light is centered at a wavelength from about 410 nm to about 480 nm.

Example Embodiment 27

The method of embodiment 21, wherein the peak intensity of the light is centered at a wavelength of about 459 nm.

Example Embodiment 28

The method of embodiment 21, wherein the ambient air is maintained at a temperature from about 90° C. to about 130° C.

Example Embodiment 29

The method of embodiment 21, wherein the ambient air is maintained at a temperature of about 120° C.

Example Embodiment 30

The method of embodiment 21, further comprising cooling the polycarbonate.

Example Embodiment 31

The method of embodiment 22, wherein evaluating said degradation comprises visually inspecting the polycarbonate.

Example Embodiment 32

The method of embodiment 22, wherein evaluating the degradation comprises measuring a degree of discoloration of the polycarbonate.

Example Embodiment 33

The method of embodiment 32, wherein measuring the degree of discoloration of the polycarbonate comprises:
 illuminating the polycarbonate with white light, a portion of the white light being transmitted through the polycarbonate; and
 generating a transmission spectrum from the portion of the white light transmitted through the polycarbonate.

Example Embodiment 34

The method of embodiment 32, wherein measuring the degree of discoloration of the transparent polycarbonate comprises:
 illuminating the transparent polycarbonate with white light, a portion of the white light being reflected from the transparent polycarbonate; and
 generating a reflectance spectrum of the portion of the white light reflected from the transparent polycarbonate.

Example Embodiment 35

The method of embodiment 22, further comprising:
 repeating the illuminating and maintaining steps for a second period of time;
 after the second period of time has elapsed, measuring a degree of discoloration of the transparent polycarbonate.

Example Embodiment 36

The method of embodiment 35, further comprising comparing the degree of discoloration measured after the first period of time with the degree of discoloration after the second period of time.

Example Embodiment 37

The method of embodiment 35, wherein the second period of time equals the first period of time in duration.

Example Embodiment 38

The method of embodiment 37, wherein the first period of time is about 100 hours in duration.

Example Embodiment 39

The method of embodiment 21, wherein the polycarbonate may be a transparent, translucent or opaque thermoplastic.

Example Embodiment 40

A method for determining a discoloration rate of a transparent polycarbonate, the method comprising:
  illuminating the transparent polycarbonate with light having a peak intensity centered at a wavelength from about 400 nm to about 500 nm and an irradiance from about 3,500 W/m$^2$ to about 120,000 W/m$^2$ for a period of time;
  maintaining ambient air surrounding the transparent polycarbonate at a temperature from about 23° C. to about 175° C. during the period of time;
  repeating the illuminating and maintaining steps for a plurality of successive periods of time; and
  after each the successive period of time, measuring a degree of discoloration of the transparent polycarbonate.

Example Embodiment 41

The method of embodiment 40, further comprising evaluating a degree of discoloration of the transparent polycarbonate after each successive period of time.

Example Embodiment 42

The method of embodiment 41, further comprising:
  repeating the illuminating, maintaining and measuring steps for a plurality of successive time periods for a plurality of different transparent polycarbonate formulations; and
  comparing the discoloration of the plurality of different transparent polycarbonate formulations with one another.

Example Embodiment 43

The method of embodiment 40, wherein all of the periods of time are equal to one another in duration.

Example Embodiment 44

The method of embodiment 40, wherein the first period of time is about 100 hours.

Example Embodiment 45

The method of embodiment 40, further comprising comparing the degree of discoloration measured after each the period of time with one another.

Example Embodiment 46

The method of embodiment 40, wherein the irradiance is from about 70,000 W/m$^2$ to about 110,000 W/m$^2$.

Example Embodiment 47

The method of embodiment 40, wherein the irradiance is about 100,000 W/m$^2$.

Example Embodiment 48

The method of embodiment 40, wherein the peak intensity of the light is centered at a wavelength from about 410 nm to about 480 nm.

Example Embodiment 49

The method of embodiment 40, wherein the peak intensity of the light is centered at a wavelength of about 459 nm.

Example Embodiment 50

The method of embodiment 40, wherein the ambient air is maintained at a temperature from about 90° C. to about 130° C.

Example Embodiment 51

The method of embodiment 40, wherein the ambient air is maintained at a temperature of about 120° C.

Example Embodiment 52

The method of embodiment 40, further comprising cooling the transparent polycarbonate.

Example Embodiment 53

The method of embodiment 41, wherein evaluating the degradation comprises visually inspecting the polycarbonate.

Example Embodiment 54

The method of embodiment 41, wherein evaluating the degradation comprises measuring a degree of discoloration of the polycarbonate.

Example Embodiment 55

The method of embodiment 54, wherein measuring the degree of discoloration of the transparent polycarbonate comprises:
  illuminating the transparent polycarbonate with white light, a portion of the white light being transmitted through the transparent polycarbonate; and
  generating a transmission spectrum from the portion of the white light transmitted through the transparent polycarbonate.

Example Embodiment 56

The method of embodiment 54, wherein measuring the degree of discoloration of the transparent polycarbonate comprises:

illuminating the transparent polycarbonate with white light, a portion of the white light being reflected from the transparent polycarbonate; and generating a reflectance spectrum of the portion of the white light reflected from the transparent polycarbonate.

Example Embodiment 57

The method according to embodiment 1, wherein the thermoplastic is translucent.

Example Embodiment 58

The method according to embodiment 1, wherein the thermoplastic is opaque.

Example Embodiment 59

The method according to embodiment 1, wherein the thermoplastic comprises polyethylene terephthalate (PET).

Example Embodiment 60

The method according to embodiment 1, wherein the thermoplastic comprises polybutylene terephthalate (PBT).

Example Embodiment 61

The method according to embodiment 1, wherein the thermoplastic comprises polyethylene napthalate (PEN).

Example Embodiment 62

The method according to embodiment 1, wherein the thermoplastic comprises polymethyl methacrylate (PMMA).

Example Embodiment 63

The method according to embodiment 1, wherein the thermoplastic comprises polystyrene (PS).

Example Embodiment 64

The method according to embodiment 1, wherein the thermoplastic comprises cyclic olefinic polymers (COP).

Example Embodiment 65

The method according to embodiment 1, wherein the thermoplastic comprises cyclic olefinic copolymers (COC).

Example Embodiment 66

The method according to embodiment 1, wherein the thermoplastic comprises polyetherimide.

Example Embodiment 67

The method according to embodiment 1, wherein the thermoplastic comprises polycarbonate.

Example Embodiment 68

The method according to embodiment 1, wherein the thermoplastic comprises polyester blends.

Example Embodiment 69

The method according to embodiment 1, wherein the thermoplastic comprises polycarbonate/polyester blends.

DETAILED DESCRIPTION

Figure 1:
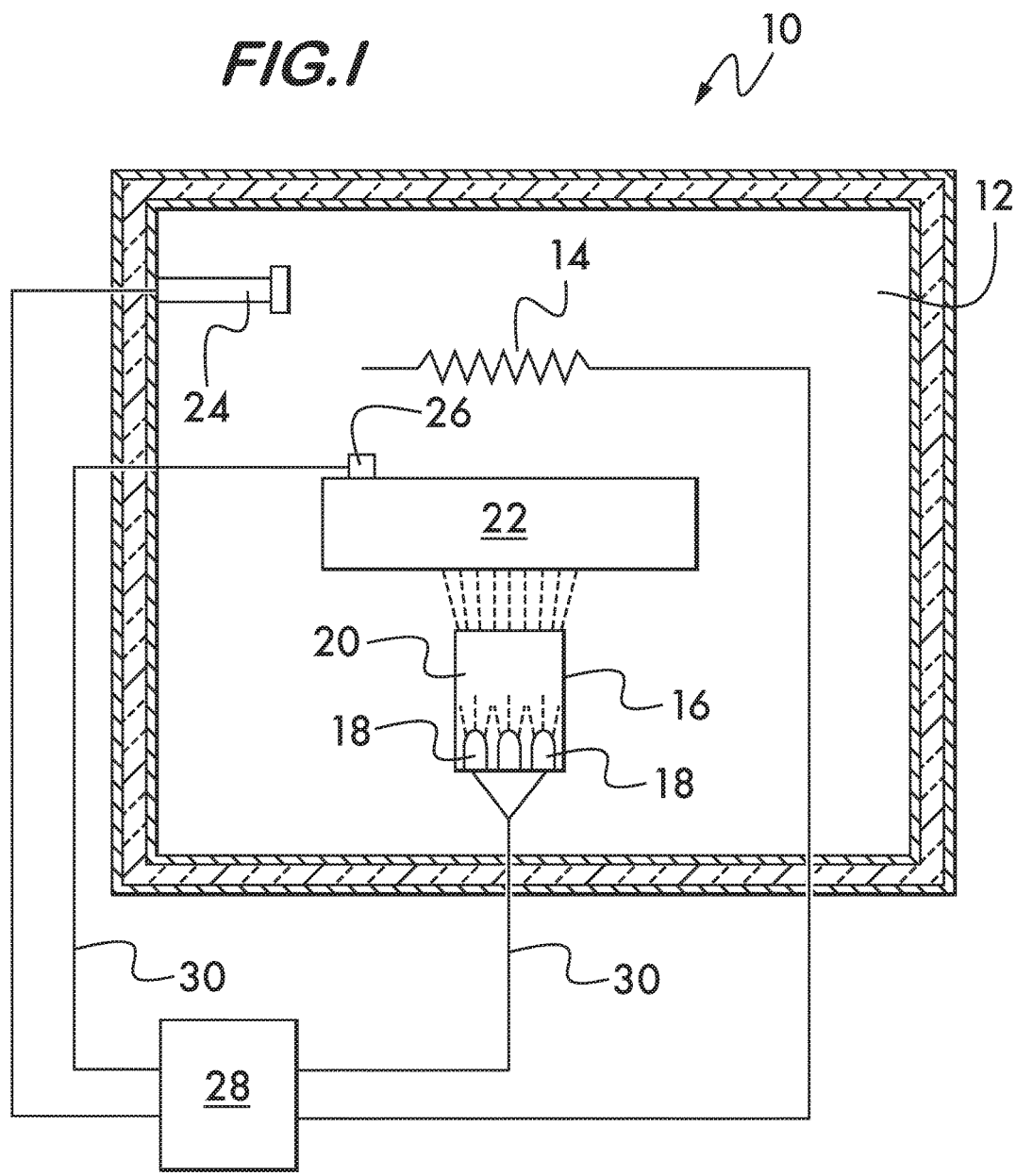
FIG. 1 is a schematic diagram illustrating an example device for executing a method for determining degradation of a thermoplastic, such as an opaque, translucent or transparent polycarbonate.

FIG. 1 shows an example apparatus 10 which is useful for determining degradation of thermoplastics, in particular, for characterizing and comparing the rate of discoloration of opaque, translucent and transparent polycarbonates. Apparatus 10 comprises an oven chamber 12 in which a heating element 14 is positioned. The heating element 14 establishes and maintains the ambient air within the chamber 12 at a desired temperature appropriate for a particular test protocol. In a practical example, the heating element 14 may be an electrical resistance heater. At least one light source 16 is also positioned within chamber 12, the light source 16 being selected to emit light over a desired frequency range appropriate to the test requirements. In a particular example, the light source 16 may comprise a plurality of LEDs 18 whose light is channeled by a silica glass waveguide 20 so as to impinge upon a thermoplastic sample 22 positioned within the chamber 12 for testing.

Temperature of the ambient air within the chamber 12 is monitored by a temperature measuring device 24 positioned within the chamber, for example, a thermometer or a thermocouple, which generates electrical signals indicative of the air temperature within the chamber. Another temperature measuring device 26 (again, for example, a thermocouple) is mounted on the thermoplastic sample 22 and used to monitor the sample temperature, which may be higher than the air temperature due to the light impinging from the light source 16. Signals from the temperature measuring devices 24 and 26 are supplied to a controller 28, which uses the temperature information to control the heating element 14 and the light source 16 during testing of the sample 22. Controller 28 may be, for example, a programmable logic controller or a computer with resident software, which, in addition to receiving and interpreting the temperature signals and controlling the operation of the light source 16 and the heating element 14, may also record and log data from the test. Communication between the various components and the controller 28 is effected in this example over dedicated communication lines 30.

Figure 2:
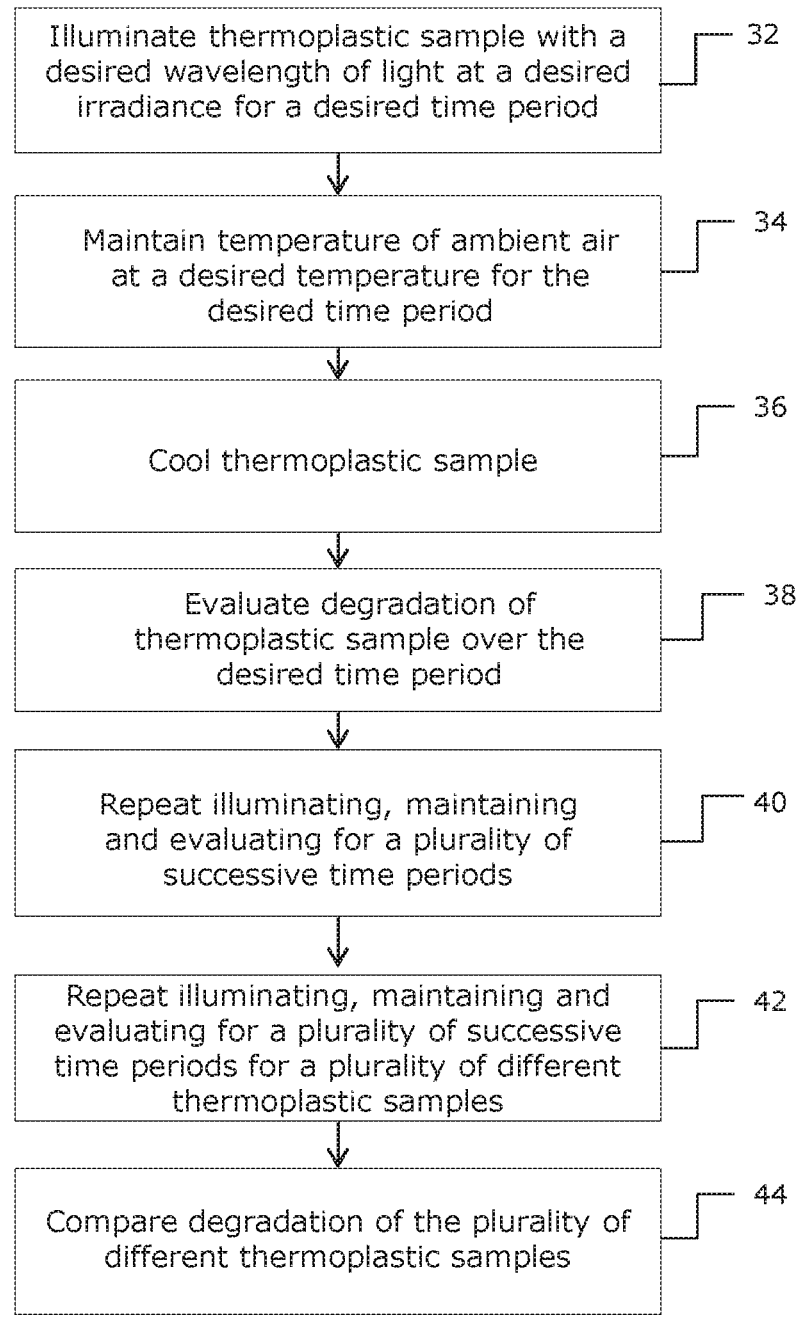
FIG. 2 is a flow chart illustrating an example method for determining degradation of thermoplastic according to the invention.

FIG. 2 is a flow chart which outlines an example method of determining degradation of opaque, translucent and transparent thermoplastics according to the invention. In this example, the thermoplastic sample, such as a transparent polycarbonate of a first formulation, is illuminated with light for a desired period of time as noted at box 32. When determining discoloration of a transparent polycarbonate for use with LED lamps for example, it has been found advantageous to use illuminating light having its peak intensity centered at a wavelength from about 400 nm to about 500 nm and having an irradiance from about 3,500 W/m$^2$ to about 120,000 W/m$^2$ (calibration for all irradiance values via an integrating sphere).

As noted in box 34, during illumination, the ambient air surrounding the sample is maintained at a desired temperature, for example, from about 23° C. to about 175° C. for the desired period of time. (The maximum ambient air temperature is generally limited by the glass transition temperature of the sample being tested.) The data derived from this test can be used to determine an instantaneous rate of degradation of the sample, as well as for comparative purposes with other samples having different formulations. Irradiance from about 70,000 W/m$^2$ to about 110,000 W/m$^2$ is also believed to be useful, as is an irradiance of about 100,000 W/m$^2$. Ambient air temperatures from about 90° C. to about 130° C. are also believed to be useful, as is an air temperature of about 120° C. as well as 130° C. Additionally, illuminating light wavelengths wherein the peak intensity of the light is centered from about 410 nm to about 480 nm (measured radiometrically) are believed to be useful, as is illuminating light having its peak intensity centered at about 459 nm (measured radiometrically). These parameters are expected to allow for an illumination time period of as much as 100 hours, resulting in a measurable discoloration of the transparent polycarbonate without destroying the sample. It is further expected that illuminating light having its peak intensity centered at about 448 nm (measured radiometrically) will be useful as well as illuminating light emitted from an LED source and centered at about 470 nm dominant wavelength (measured photometrically).

It may also be desirable to prevent excessive heat build-up in the sample which could destroy it. Excessive heat build-up may be avoided by cooling the sample during illumination. Cooling of the sample, as noted in box 36, may be accomplished, for example, by providing a separation distance between the sample and the light source sufficient to permit circulation of the ambient air around the sample and thereby allow convective cooling. Other methods of cooling, such as forced air cooling using a fan for example, are also feasible.

The step of evaluating the degradation of the sample is noted in box 38. This evaluation step may be accomplished, for example, by a simple visual observation of the samples, or photographs of the samples. Measurement techniques are also useful, as explained in detail below with reference to FIGS. 3 and 4.

As described in box 40, the illuminating, maintaining and evaluating steps may be repeated for a plurality of successive time periods to provide, for example, the rate of discoloration of a polycarbonate sample as a function of time over which it is illuminated. This may show, for example, whether the rate of discoloration increases, decreases, or remains the same over time as it is exposed to the light. The successive time periods may be equal to one another.

As noted in boxes 42 and 44, the method comprising the illuminating, maintaining and evaluating steps may be repeated for a plurality of successive time periods for a plurality of different thermoplastic samples having different formulations. This will permit a comparative evaluation between different polycarbonate formulations to determine their relative suitability for various applications, such as for use with LED lamps as noted below.

Figure 3:
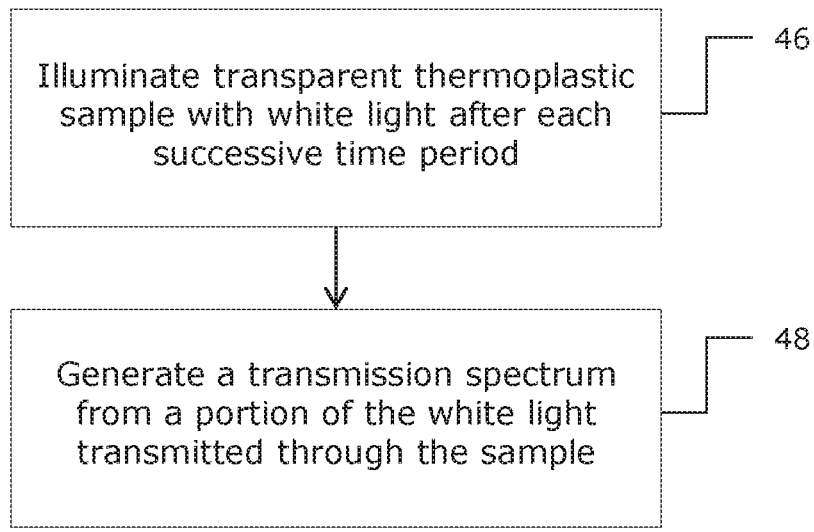
FIGS. 3 and 4 are flow charts illustrating example methods for measuring a degree of discoloration of transparent thermoplastic samples.

As shown in boxes 46 and 48 of FIG. 3, measurement of the transparent thermoplastic degradation, in this example discoloration of the transparent polycarbonate, is effected by illuminating the sample with white light after the desired time period has elapsed, and generating a transmission spectrum from a portion of the white light transmitted through the sample. In an alternate method outlined in boxes 50 and 52 of FIG. 4, the sample is illuminated with white light after the desired time period has elapsed and a reflectance spectrum is generated from the portion of the white light reflected from the sample. Either spectrum is expected to provide a useful measure of the discoloration of a transparent thermoplastic such as polycarbonate. The measurement method shown in FIG. 4 could also be effectively applied to opaque and translucent thermoplastics.

Figure 4:
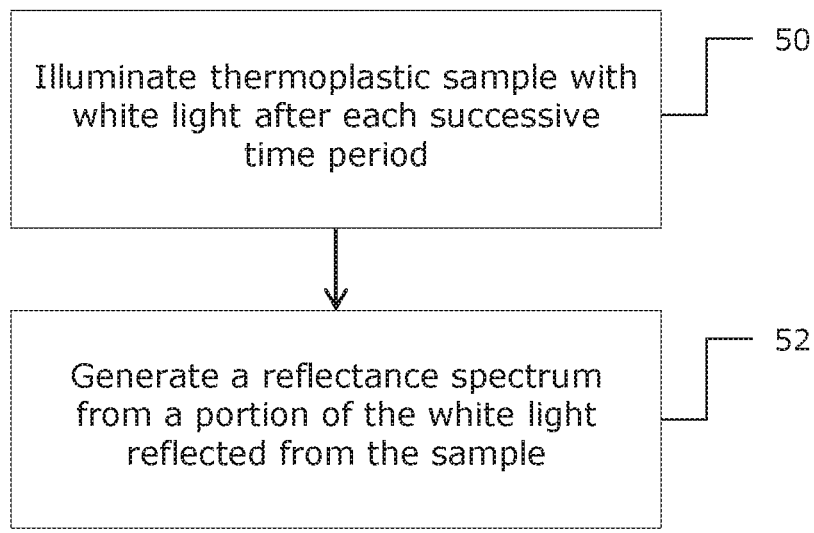

The example method outlined in FIGS. 2-4 may be used to gather data on a plurality of different polycarbonate formulations and then compare the discoloration rates of the various different formulations to determine which might be suitable for use in LED lighting, those sample polycarbonate formulations having the slowest discoloration rate being advantageous. Testing methods using the parameters outlined herein have permitted illumination time periods of 100 hours, and as many as 15 successive 100 hour time periods have been used to evaluate numerous different samples to determine and compare their discoloration rates.

Various polycarbonate formulations to which the example method may be applied are described below.

Definitions

Ranges articulated within this disclosure, e.g. numerics/values, shall include disclosure for possession purposes and claim purposes of the individual points within the range, sub-ranges, and combinations thereof.

Various combinations of elements of this disclosure are encompassed by this invention, e.g. combinations of elements from dependent claims that depend upon the same independent claim.

The word "about" should be given its ordinary and accustomed meaning and should be relative to the word or phrase(s) that it modifies. In the context of pKa, the word "about" as it pertains to pKa can equal the value of the numeric or can equal in the range of +/−0.1 of the pKa unit, e.g. pKa of about 8.3 can include 8.2, and the word "about" as it pertains to branching level can equal the value of the numeric or can equal in the range +/−0.05% of the branching level, e.g. about 1% can encompass 0.95%. The delineation of the word about in the context pKa and branching level should not in any way limit the ordinary and accustomed meaning of the word "about" for other language/numerics that the word "about" modifies.

The pKa values used in the model for the end-capping agents are listed in Table 1 below:

TABLE 1

| End-capping agent | pKa* |
| --- | --- |
| p-cyanophenol | 8.2 |
| p-methyl-hydroxy benzoate | 8.4 |
| phenol | 9.9 |
| p-t-butylphenol | 10.2 |
| p-methoxyphenol | 10.4 |
| p-cumylphenol | 10.5 |

*pKa values for all of the end-capping agents but p-t-butyl phenol and p-cumylphenol were obtained from the following reference: J. AM. CHEM. SOC. 2002, 6424. The values chosen in the reference were listed in the S7 category in Table 3 of the reference. The pKa value for p-t-butylphenol was obtained from the following reference: Journal of Molecular Structure: THEOCHEM 805, 2006, 31. The pKa for methyl-p-hydroxybenzoate was obtained from the following reference: Chromatographia Vol. 39, No. 5/6, September 1994. The pKa value for p-cumylphenol was approximated based on the values of similar structures.

Polycarbonate Material/Structural Backbone of the Composition

In one embodiment, the plastic material of the plastic composition can comprise a polycarbonate. Descriptions of the various types of polycarbonates are articulated below, but should not be construed as limiting.

Various types of polycarbonates that have a repeating structural background of the following formula:

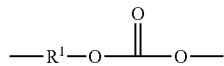

can be utilized.

The selection of a polycarbonate backbone of choice depends on many factors such as end use and other factors understood by one of ordinary skill the art.

In one embodiment, the polycarbonates have repeating structural carbonate units of the formula (1):

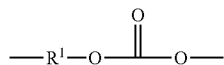

(1)

wherein greater than or equal to 60 percent of the total number of $R^1$ groups contain aromatic organic groups and the balance thereof are aliphatic, alicyclic, or aromatic groups.

In another embodiment, the polycarbonate is derived from bisphenol-A.

In another embodiment, each $R^1$ group is a divalent aromatic group, for example derived from an aromatic dihydroxy compound of the formula (2):

$$HO-A^1-Y^1-A^2-OH \quad (2)$$

wherein each of $A^1$ and $A^2$ is a monocyclic divalent arylene group, and Y1 is a single bond or a bridging group having one or two atoms that separate $A^1$ from $A^2$. In an exemplary embodiment, one atom separates $A^1$ from $A^2$. In another embodiment, when each of $A^1$ and $A^2$ is phenylene, $Y^1$ is para to each of the hydroxyl groups on the phenylenes. Illustrative non-limiting examples of groups of this type are —O—, —S—, —S(O)—, —S(O)$_2$—, —C(O)—, methylene, cyclohexyl-methylene, 2-[2.2.1]-bicycloheptylidene, ethylidene, isopropylidene, neopentylidene, cyclohexylidene, cyclopentadecylidene, cyclododecylidene, and adamantylidene. The bridging group $Y^1$ can be a hydrocarbon group or a saturated hydrocarbon group such as methylene, cyclohexylidene, or isopropylidene.

Included within the scope of formula (2) are bisphenol compounds of general formula (3):

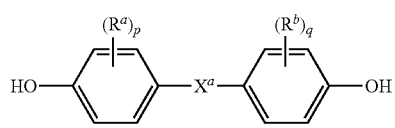

(3)

wherein $R^a$ and $R^b$ each represent a halogen atom or a monovalent hydrocarbon group and can be the same or different; p and q are each independently integers of 0 to 4; and $X^a$ represents a single bond or one of the groups of formulas (4) or (5):

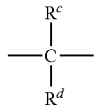

(4)

(5)

wherein $R^c$ and $R^d$ are each independently hydrogen, $C_{1-12}$ alkyl, $C_{1-12}$ cycloalkyl, $C_{7-12}$ arylalkyl, $C_{1-12}$ heteroalkyl, or cyclic $C_{7-12}$ heteroarylalkyl, and $R^e$ is a divalent $C_{1-12}$ hydrocarbon group. In particular, $R^c$ and $R^d$ are each the same hydrogen or $C_{1-4}$ alkyl group, specifically the same $C_{1-3}$ alkyl group, even more specifically, methyl.

In an embodiment, $R^c$ and $R^d$ taken together represent a $C_{3-20}$ cyclic alkylene group or a heteroatom-containing $C_{3-20}$ cyclic alkylene group comprising carbon atoms and heteroatoms with a valency of two or greater. These groups can be in the form of a single saturated or unsaturated ring, or a fused polycyclic ring system wherein the fused rings are saturated, unsaturated, or aromatic. A specific heteroatom-containing cyclic alkylene group comprises at least one heteroatom with a valency of 2 or greater, and at least two carbon atoms. Exemplary heteroatoms in the heteroatom-containing cyclic alkylene group include —O—, —S—, and —N(Z)—, where Z is a substituent group selected from hydrogen, hydroxy, $C_{1-12}$ alkyl, $C_{1-12}$ alkoxy, or $C_{1-12}$ acyl.

In a specific exemplary embodiment, $X^a$ is a substituted $C_{3-18}$ cycloalkylidene of the formula (6):

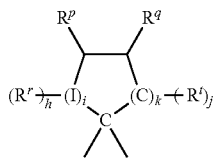

(6)

wherein each $R^r$, $R^p$, $R^q$, and $R^t$ is independently hydrogen, halogen, oxygen, or $C_{1-12}$ organic group; I is a direct bond, a carbon, or a divalent oxygen, sulfur, or —N(Z)— wherein Z is hydrogen, halogen, hydroxy, $C_{1-12}$ alkyl, $C_{1-12}$alkoxy, or $C_{1-12}$ acyl; h is 0 to 2, j is 1 or 2, i is an integer of 0 or 1, and k is an integer of 0 to 3, with the proviso that at least two of $R^r$, $R^p$, $R^q$, and $R^t$ taken together are a fused cycloaliphatic, aromatic, or heteroaromatic ring. It will be understood that where the fused ring is aromatic, the ring as shown in formula (6) will have an unsaturated carbon-carbon linkage where the ring is fused. When k is 1 and i is 0, the ring as shown in formula (6) contains 4 carbon atoms, when k is 2, the ring as shown contains 5 carbon atoms, and when k is 3, the ring contains 6 carbon atoms. In one embodiment, two adjacent groups (e.g., $R^q$ and $R^t$ taken together) form an aromatic group, and in another embodiment, $R^q$ and $R^t$ taken together form one aromatic group and $R^r$ and $R^p$ taken together form a second aromatic group.

Non-limiting examples of dihydroxy compounds that can provide polycarbonates with Tgs greater than 170° C. include 3,3-bis(4-hydroxyphenyl)-2-phenylisoindolin-1-one (PPPBP), 1,1-bis(4-hydroxyphenyl)-3,3,5-trimethylcyclohexane) (Bisphenol TMC), 4,4'-(1-phenylethane-1,1-diyl) diphenol (bisphenol AP) as well as adamantyl containing aromatic dihydroxy compounds and fluorene containing aromatic dihydroxy compounds.

Specific example of dihydroxy compounds of formula (2) can be the following formula (7):

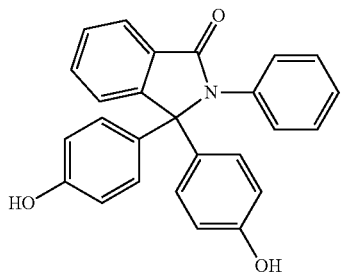

(7)

(also known as 3,3-bis(4-hydroxyphenyl)-2-phenylisoindolin-1-one (PPPBP)) also known as 2-phenyl-3,3-bis(4-hydroxyphenyl)phthalimidine.

Alternatively, the dihydroxy compounds of formula (2) may be the following formula (8):

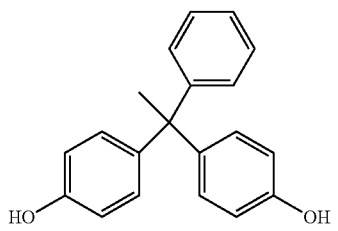

(8)

(also known as 4,4'-(1-phenylethane-1,1-diyl)diphenol (bisphenol AP) also known as 1,1-bis(4-hydroxyphenyl)-1-phenylethane).

Alternatively, the dihydroxy compounds of formula (2) may be the following formula (9):

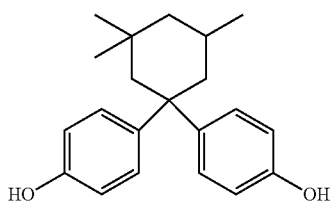

(9)

4,4'-(3,3,5-trimethylcyclohexane-1,1-diyl)diphenol (bisphenol TMC) also known as 1,1-bis(4-hydroxyphenyl)-3,3,5-trimethylcyclohexane). Examples of adamantyl containing aromatic dihydroxy compounds and fluorene containing aromatic dihydroxy compounds are set forth in Formulas (A) and (B) respectively.

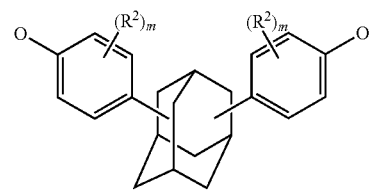

(A)

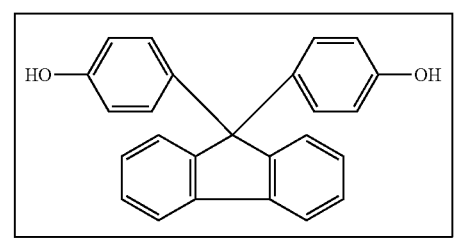

(B)

Another possible polycarbonate with high Tg is set forth in formula (C):

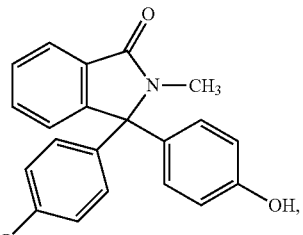

(C)

A polycarbonate can have a bisphenol of formula (D) as a repeating monomer unit therein:

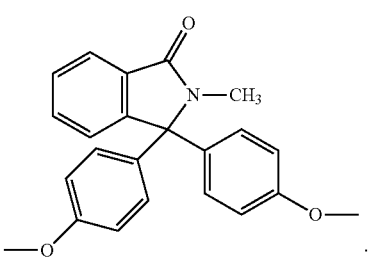

(D)

When k is 3 and i is 0, bisphenols containing substituted or unsubstituted cyclohexane units are used, for example bisphenols of formula (10):

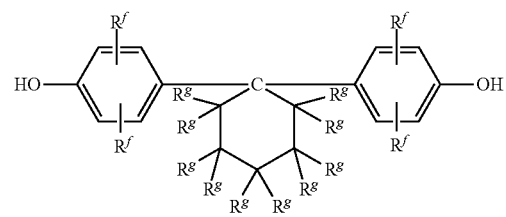

(10)

wherein each $R^f$ is independently hydrogen, $C_{1-12}$ alkyl, or halogen; and each $R^g$ is independently hydrogen or $C_{1-12}$ alkyl. The substituents can be aliphatic or aromatic, straight chain, cyclic, bicyclic, branched, saturated, or unsaturated. Such cyclohexane-containing bisphenols, for example the reaction product of two moles of a phenol with one mole of a hydrogenated isophorone, are useful for making polycarbonate polymers with high glass transition temperatures and high heat distortion temperatures. Cyclohexyl bisphenol containing polycarbonates, or a combination comprising at least one of the foregoing with other bisphenol polycarbonates, are supplied by Bayer Co. under the APEC® trade name.

Other useful dihydroxy compounds having the formula HO—$R^1$—OH include aromatic dihydroxy compounds of formula (11):

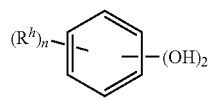

(11)

wherein each $R^h$ is independently a halogen atom, a $C_{1-10}$ hydrocarbyl such as a $C_{1-10}$ alkyl group, a halogen substituted $C_{1-10}$ hydrocarbyl such as a halogen-substituted $C_{1-10}$ alkyl group, and n is 0 to 4. The halogen is usually bromine.

Some illustrative examples of dihydroxy compounds include the following: 4,4'-dihydroxybiphenyl, 1,6-dihydroxynaphthalene, 2,6-dihydroxynaphthalene, bis(4-hydroxyphenyl)methane, bis(4-hydroxyphenyl)diphenylmethane, bis(4-hydroxyphenyl)-1-naphthylmethane, 1,2-bis(4-hydroxyphenyl)ethane, 1,1-bis(4-hydroxyphenyl)-1-phenylethane, 2-(4-hydroxyphenyl)-2-(3-hydroxyphenyl) propane, bis(4-hydroxyphenyl)phenylmethane, 2,2-bis(4-hydroxy-3-bromophenyl)propane, 1,1-bis (hydroxyphenyl) cyclopentane, 1,1-bis(4-hydroxyphenyl)cyclohexane, 1,1-bis(4-hydroxyphenyl)isobutene, 1,1-bis(4-hydroxyphenyl) cyclododecane, trans-2,3-bis(4-hydroxyphenyl)-2-butene, 2,2-bis(4-hydroxyphenyl)adamantine, alpha, alpha'-bis(4-hydroxyphenyl)toluene, bis(4-hydroxyphenyl)acetonitrile, 2,2-bis(3-methyl-4-hydroxyphenyl)propane, 2,2-bis(3-ethyl-4-hydroxyphenyl)propane, 2,2-bis(3-n-propyl-4-hydroxyphenyl)propane, 2,2-bis(3-isopropyl-4-hydroxyphenyl)propane, 2,2-bis(3-sec-butyl-4-hydroxyphenyl)propane, 2,2-bis(3-t-butyl-4-hydroxyphenyl)propane, 2,2-bis(3-cyclohexyl-4-hydroxyphenyl)propane, 2,2-bis(3-allyl-4-hydroxyphenyl)propane, 2,2-bis(3-methoxy-4-hydroxyphenyl)propane, 2,2-bis(4-hydroxyphenyl)hexafluoropropane, 1,1-dichloro-2,2-bis(4-hydroxyphenyl)ethylene, 1,1-dibromo-2,2-bis(4-hydroxyphenyl)ethylene, 1,1-dichloro-2,2-bis(5-phenoxy-4-hydroxyphenyl)ethylene, 4,4'-dihydroxybenzophenone, 3,3-bis(4-hydroxyphenyl)-2-butanone, 1,6-bis(4-hydroxyphenyl)-1,6-hexanedione, ethylene glycol bis (4-hydroxyphenyl)ether, bis(4-hydroxyphenyl)ether, bis(4-hydroxyphenyl)sulfide, bis(4-hydroxyphenyl)sulfoxide, bis (4-hydroxyphenyl)sulfone, 9,9-bis(4-hydroxyphenyl) fluorine, 2,7-dihydroxypyrene, 6,6'-dihydroxy-3,3,3',3'-tetramethylspiro(bis)indane ("spirobiindane bisphenol"), 3,3-bis(4-hydroxyphenyl)phthalide, 2,6-dihydroxydibenzo-p-dioxin, 2,6-dihydroxythianthrene, 2,7-dihydroxyphenoxathin, 2,7-dihydroxy-9,10-dimethylphenazine, 3,6-dihydroxydibenzofuran, 3,6-dihydroxydibenzothiophene, and 2,7-dihydroxycarbazole, resorcinol, substituted resorcinol compounds such as 5-methyl resorcinol, 5-ethyl resorcinol, 5-propyl resorcinol, 5-butyl resorcinol, 5-t-butyl resorcinol, 5-phenyl resorcinol, 5-cumyl resorcinol, 2,4,5,6-tetrafluoro resorcinol, 2,4,5,6-tetrabromo resorcinol, or the like; catechol; hydroquinone; substituted hydroquinones such as 2-methyl hydroquinone, 2-ethyl hydroquinone, 2-propyl hydroquinone, 2-butyl hydroquinone, 2-t-butyl hydroquinone, 2-phenyl hydroquinone, 2-cumyl hydroquinone, 2,3, 5,6-tetramethyl hydroquinone, 2,3,5,6-tetra-t-butyl hydroquinone, 2,3,5,6-tetrafluoro hydroquinone, 2,3,5,6-tetrabromo hydroquinone, and the like, as well as combinations comprising at least one of the foregoing dihydroxy compounds.

Specific examples of bisphenol compounds that can be represented by formula (2) include 1,1-bis(4-hydroxyphenyl) methane, 1,1-bis(4-hydroxyphenyl) ethane, 2,2-bis(4-hydroxyphenyl) propane (hereinafter "bisphenol A" or "BPA"), 2,2-bis(4-hydroxyphenyl) butane, 2,2-bis(4-hydroxyphenyl) octane, 1,1-bis(4-hydroxyphenyl) propane, 1,1-bis(4-hydroxyphenyl) n-butane, 2,2-bis(4-hydroxy-1-methylphenyl) propane, 1,1-bis(4-hydroxy-t-butylphenyl) propane, 3,3-bis(4-hydroxyphenyl) phthalimidine, 2-phenyl-3,3-bis(4-hydroxyphenyl) phthalimidine (PPPBP), and 1,1-bis(4-hydroxy-3-methylphenyl)cyclohexane (DMBPC). Combinations comprising at least one of the foregoing dihydroxy compounds can also be used.

"Polycarbonate" as used herein includes homopolycarbonates, copolymers comprising different $R^1$ moieties in the carbonate (also referred to herein as "copolycarbonates"), and copolymers comprising carbonate units and other types of polymer units, such as ester units. In one specific embodiment, the polycarbonate is a linear homopolymer or copolymer comprising units derived from bisphenol A, in which each of $A^1$ and $A^2$ is p-phenylene and is isopropylidene in formula (2). More specifically, greater than or equal to 60%, particularly greater than or equal to 80% of the $R^1$ groups in the polycarbonate are derived from bisphenol A.

Another specific type of copolymer is a polyester carbonate, also known as a polyester-polycarbonate. Such copolymers further contain, in addition to recurring carbonate chain units of the formula (1), repeating units of formula (9):

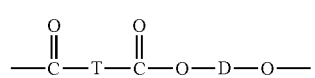

(9)

wherein D is a divalent group derived from a dihydroxy compound, and can be, for example, a $C_2$-$C_{10}$ alkylene group, a $C_6$-$C_{20}$ alicyclic group, a $C_6$-$C_{20}$ aromatic group or a polyoxyalkylene group in which the alkylene groups contain 2 to 6 carbon atoms, specifically 2, 3, or 4 carbon atoms; and T divalent group derived from a dicarboxylic acid, and can be, for example, a $C_2$-$C_{10}$ alkylene group, a $C_6$-$C_{20}$ alicyclic group, a $C_6$-$C_{20}$ alkyl aromatic group, or a $C_6$-$C_{20}$ aromatic group.

In one embodiment, D is a $C_2$ to $C_{30}$ alkylene group having a straight chain, branched chain, or cyclic (including polycyclic) structure. In another embodiment, D is derived from an aromatic dihydroxy compound of formula (3) above. In another embodiment, D is derived from an aromatic dihydroxy compound of formula (8) above.

Examples of aromatic dicarboxylic acids that can be used to prepare the polyester units include isophthalic or terephthalic acid, 1,2-di(p-carboxyphenyl)ethane, 4,4'-dicarboxydiphenyl ether, 4,4'-bisbenzoic acid, and combinations comprising at least one of the foregoing acids. Acids containing fused rings can also be present, such as in 1,4-, 1,5-, or 2,6-naphthalenedicarboxylic acids. Specific dicarboxylic acids are terephthalic acid, isophthalic acid, naphthalene dicarboxylic acid, cyclohexane dicarboxylic acid, or combinations thereof. A specific dicarboxylic acid comprises a combination of isophthalic acid and terephthalic acid wherein the weight ratio of isophthalic acid to terephthalic acid is 91:9 to 2:98. In another specific embodiment, D is a $C_{2-6}$ alkylene group and T is p-phenylene, m-phenylene, naphthalene, a divalent cycloaliphatic group, or a combination thereof. This class of polyester includes the poly(alkylene terephthalates).

The molar ratio of ester units to carbonate units in the copolymers can vary broadly, for example 1:99 to 99:1, specifically 10:90 to 90:10, more specifically 25:75 to 75:25, depending on the desired properties of the final composition.

In a specific embodiment, the polyester unit of a polyester-polycarbonate can be derived from the reaction of a combination of isophthalic and terephthalic diacids (or derivatives thereof) with resorcinol. In another specific embodiment, the polyester unit of a polyester-polycarbonate is derived from the reaction of a combination of isophthalic acid and terephthalic acid with bisphenol-A. In a specific embodiment, the polycarbonate units are derived from bisphenol A. In another specific embodiment, the polycarbonate units are derived from resorcinol and bisphenol A in a molar ratio of resorcinol carbonate units to bisphenol A carbonate units of 1:99 to 99:1.

A specific example of a polycarbonate-polyester is a copolycarbonate-polyester-polysiloxane terpolymer comprising carbonate units of formula (1), ester units of formula (9), and polysiloxane (also referred to herein as "polydiorganosiloxane") units of formula (10):

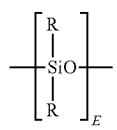

(10)

wherein each occurrence of R is same or different, and is a $C_{1-13}$ monovalent organic group. For example, R may independently be a $C_{1-13}$ alkyl group, $C_{1-13}$ alkoxy group, $C_{2-13}$ alkenyl group, $C_{2-13}$ alkenyloxy group, $C_{3-6}$ cycloalkyl group, $C_{3-6}$ cycloalkoxy group, $C_{6-14}$ aryl group, $C_{6-10}$ aryloxy group, $C_{7-13}$ arylalkyl group, $C_{7-13}$ arylalkoxy group, $C_{7-13}$ alkylaryl group, or $C_{7-13}$ alkylaryloxy group. The foregoing groups may be fully or partially halogenated with fluorine, chlorine, bromine, or iodine, or a combination thereof. Combinations of the foregoing R groups may be used in the same copolymer. In an embodiment, the polysiloxane comprises R groups that have a minimum hydrocarbon content. In a specific embodiment, an R group with a minimum hydrocarbon content is a methyl group.

The value of E in formula (10) may vary widely depending on the type and relative amount of each component in the plastic (e.g., thermoplastic) composition, the desired properties of the composition, and like considerations. Herein, E has an average value of 5 to 200, with the specific amount chosen so that a 1.0 mm thick plaque of the plastic composition (i.e., plastic material, coated conversion material(s), any additive(s)) has a transparency (% T) of greater than or equal to 30%. It is readily understood by an artisan that the E value is chosen (e.g., adjusted such as when the amount of siloxane in the material and when the siloxane is introduced to form the material and/or the process for making the material) to achieve a balance between transparency, flame retardancy, and impact. In an embodiment, E has an average value of 16 to 50, specifically 20 to 45, and more specifically 25 to 45. In another embodiment, E has an average value of 4 to 15, specifically 5 to 15, more specifically 6 to 15, and still more specifically 7 to 12.

In an embodiment, polydiorganosiloxane units are derived from dihydroxy aromatic compound of formula (11):

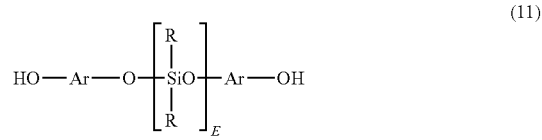

(11)

wherein E is as defined above; each R may independently be the same or different, and is as defined above; and each Ar may independently be the same or different, and is a substituted or unsubstituted $C_{6-30}$ arylene group, wherein the bonds are directly connected to an aromatic moiety. Suitable Ar groups in formula (11) may be derived from a $C_{6-30}$ dihydroxy aromatic compound, for example a dihydroxy aromatic compound of formula (2), (3), (7), or (8) above. Combinations comprising at least one of the foregoing dihydroxy aromatic compounds may also be used. Examples of dihydroxy aromatic compounds include resorcinol (i.e., 1,3-dihydroxybenzene), 4-methyl-1,3-dihydroxybenzene, 5-methyl-1,3-dihydroxybenzene, 4,6-dimethyl-1,3-dihydroxybenzene, 1,4-dihydroxybenzene, 1,1-bis(4-hydroxyphenyl) methane, 1,1-bis(4-hydroxyphenyl) ethane, 2,2-bis(4-hydroxyphenyl) propane, 2,2-bis(4-hydroxyphenyl) butane, 2,2-bis(4-hydroxyphenyl) octane, 1,1-bis(4-hydroxyphenyl) propane, 1,1-bis(4-hydroxyphenyl) n-butane, 2,2-bis(4-hydroxy-1-methylphenyl) propane, 1,1-bis(4-hydroxyphenyl) cyclohexane, bis(4-hydroxyphenyl sulfide), and 1,1-bis(4-hydroxy-t-butylphenyl) propane. Combinations comprising at least one of the foregoing dihydroxy compounds may also be used. In an embodiment, the dihydroxy aromatic compound is unsubstituted, or is not substituted with non-aromatic hydrocarbon-containing substituents such as, for example, alkyl, alkoxy, or alkylene substituents.

In a specific embodiment, where Ar is derived from resorcinol, the polydiorganosiloxane repeating units are derived from dihydroxy aromatic compounds of formula (12):

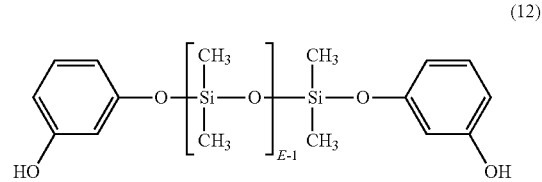

(12)

or, where Ar is derived from bisphenol-A, from dihydroxy aromatic compounds of formula (13):

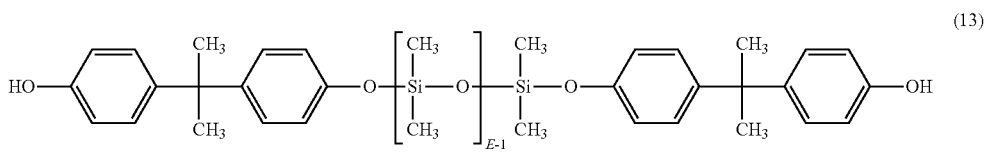
(13)

wherein E is as defined above.

In another embodiment, polydiorganosiloxane units are derived from dihydroxy aromatic compound of formula (14):

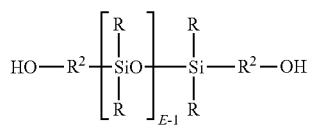
(14)

wherein R and E are as described above, and each occurrence of $R^2$ is independently a divalent $C_{1-30}$ alkylene or $C_{7-30}$ arylene-alkylene, and wherein the polymerized polysiloxane unit is the reaction residue of its corresponding dihydroxy aromatic compound. In a specific embodiment, where $R^2$ is $C_{7-30}$ arylene-alkylene, the polydiorganosiloxane units are derived from dihydroxy aromatic compound of formula (15):

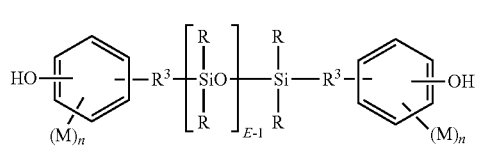
(15)

wherein R and E are as defined above. Each $R^3$ is independently a divalent $C_{2-8}$ aliphatic group. Each M may be the same or different, and may be a halogen, cyano, nitro, $C_{1-8}$ alkylthio, $C_{1-8}$ alkyl, $C_{1-8}$ alkoxy, $C_{2-8}$ alkenyl, $C_{2-8}$ alkenyloxy group, $C_{3-8}$ cycloalkyl, $C_{3-8}$ cycloalkoxy, $C_{6-10}$ aryl, $C_{6-10}$ aryloxy, $C_{7-12}$ arylalkyl, $C_{7-12}$ arylalkoxy, $C_{7-12}$ alkylaryl, or $C_{7-12}$ alkylaryloxy, wherein each n is independently 0, 1, 2, 3, or 4.

In an embodiment, M is bromo or chloro, an alkyl group such as methyl, ethyl, or propyl, an alkoxy group such as methoxy, ethoxy, or propoxy, or an aryl group such as phenyl, chlorophenyl, or tolyl; $R^3$ is a dimethylene, trimethylene or tetramethylene group; and R is a $C_{1-8}$ alkyl, haloalkyl such as trifluoropropyl, cyanoalkyl, or aryl such as phenyl, chlorophenyl or tolyl. In another embodiment, R is methyl, or a combination of methyl and trifluoropropyl, or a combination of methyl and phenyl. In still another embodiment, M is methoxy, n is 0 or 1, $R^3$ is a divalent $C_{1-3}$ aliphatic group, and R is methyl.

In a specific embodiment, the polydiorganosiloxane units are derived from a dihydroxy aromatic compound of formula (16):

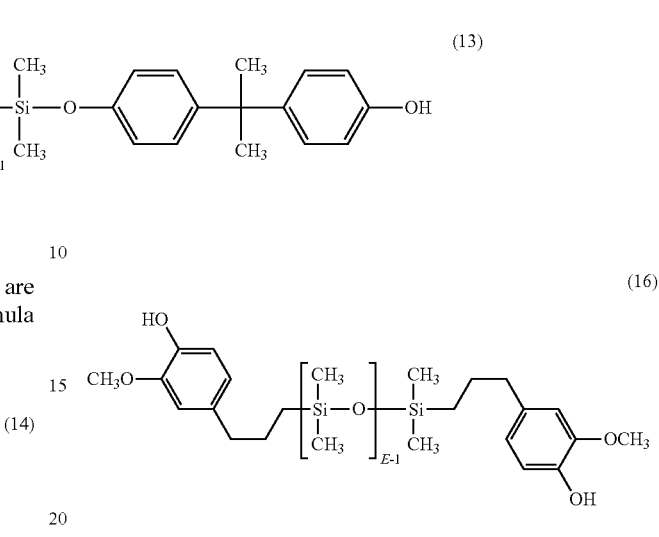
(16)

wherein E is as described above.

In another specific embodiment, the polydiorganosiloxane units are derived from dihydroxy aromatic compound of formula (17):

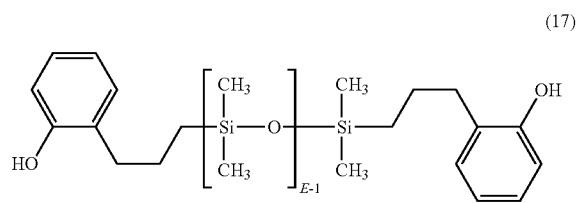
(17)

wherein E is as defined above.

Dihydroxy polysiloxanes typically can be made by functionalizing a substituted siloxane oligomer of formula (18):

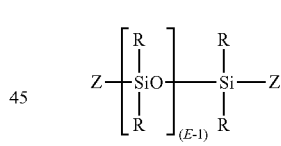
(18)

wherein R and E are as previously defined, and Z is H, halogen (Cl, Br, I), or carboxylate. Examples of carboxylates include acetate, formate, benzoate, and the like. In an exemplary embodiment, where Z is H, compounds of formula (18) may be prepared by platinum catalyzed addition with an aliphatically unsaturated monohydric phenol. Examples of aliphatically unsaturated monohydric phenols include eugenol, 2-allylphenol, 4-allylphenol, 4-allyl-2-methylphenol, 4-allyl-2-phenylphenol, 4-allyl-2-bromophenol, 4-allyl-2-t-butoxyphenol, 4-phenyl-2-allylphenol, 2-methyl-4-propenylphenol, 2-allyl-4,6-dimethylphenol, 2-allyl-4-bromo-6-methylphenol, 2-allyl-6-methoxy-4-methylphenol, and 2-allyl-4,6-dimethylphenol. Combinations comprising at least one of the foregoing may also be used. Where Z is halogen or carboxylate, functionalization may be accomplished by reaction with a dihydroxy aromatic compound of formulas (2), (3), (7), (8), or a combination comprising at least one of the foregoing dihydroxy aromatic compounds. In an embodiment, compounds of formula (12)

may be formed from an alpha, omega-bisacetoxypolydiorangonosiloxane and a dihydroxy aromatic compound under phase transfer conditions.

In some embodiments a copolycarbonate terpolymer can be used. Specific copolycarbonate terpolymers include those with polycarbonate units of formula (1) wherein is a $C_{6-30}$ arylene group, polysiloxane units derived from siloxane diols of formula (13), (16) or (17), and polyester units wherein T is a $C_{6-30}$ arylene group. In an embodiment, T is derived from isophthalic and/or terephthalic acid, or reactive chemical equivalents thereof. In another embodiment, $R^1$ is derived from the carbonate reaction product of a resorcinol of formula (8), or a combination of a resorcinol of formula (8) and a bisphenol of formula (4).

The relative amount of each type of unit in the foregoing terpolymer will depend on the desired properties of the terpolymer, and are readily determined by one of ordinary skill in the art without undue experimentation, using the guidelines provided herein. For example, the polycarbonate-polyester-polysiloxane terpolymer can comprise siloxane units in an amount of 0.1 to 25 weight percent (wt %), specifically 0.2 to 10 wt %, more specifically 0.2 to 6 wt %, even more specifically 0.2 to 5 wt %, and still more specifically 0.25 to 2 wt %, based on the total weight of the polycarbonate-polyester-polysiloxane terpolymer, with the proviso that the siloxane units are provided by polysiloxane units covalently bonded in the polymer backbone of the polycarbonate-polyester-polysiloxane terpolymer. The polycarbonate-polyester-polysiloxane terpolymer can further comprise 0.1 to 49.85 wt % carbonate units, 50 to 99.7 wt % ester units, and 0.2 to 6 wt % polysiloxane units, based on the total weight of the polysiloxane units, ester units, and carbonate units. Alternatively, the polycarbonate-polyester-polysiloxane terpolymer comprises 0.25 to 2 wt % polysiloxane units, 60 to 96.75 wt % ester units, and 3.25 to 39.75 wt % carbonate units, based on the total weight of the polysiloxane units, ester units, and carbonate units. The specific amount of terpolymer and the composition of the terpolymer will be chosen so that a 1.0 mm thick plaque of the composition transparency (% T) of greater than or equal to 30%.

In a further embodiment, a method of making an article of manufacture that has a V0 94 rating at a thickness of 2.0 mm (specifically at a thickness of 1.5 mm) comprises: (a) providing a polycarbonate, wherein the polycarbonate has a repeating structural background of the following formula

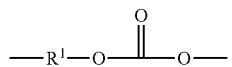

wherein greater than or equal to 60 percent of the total number of $R^1$ groups contain aromatic organic groups and the balance thereof are aliphatic, alicyclic, or aromatic groups; an end capping agent; a branching agent; (b) selecting the end-capping agent based upon the molecular weight of the polycarbonate and the branching level imparted by the branching agent, wherein the MVR of the polycarbonate is 1 to 15 cubic centimeter per 10 minutes ($cm^3$/10 min) and wherein the pKa of the end-capping agent is 8.3 to 11; (c) forming a polycarbonate containing the end-capping agent and the branching that has a peak melt viscosity of greater than or equal to 8,000 poise when measured using a parallel plate melt rheology test at a heating rate of 10° C./min at a temperature of 350° C. to 450° C.; and (d) blending a conversion material and a flame retardant with the formed polycarbonate.

The peak melt viscosity can be greater than or equal to 25,000 poise when measured using a parallel plate melt rheology test at a heating rate of 10° C./min at a temperature of 350° C. to 450° C.

In another embodiment, the composition comprises: a flame retardant; a conversion material; a polycarbonate, wherein the polycarbonate has a repeating structural background of the following formula

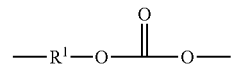

wherein greater than or equal to 60 percent of the total number of $R^1$ groups contain aromatic organic groups and the balance thereof are aliphatic, alicyclic, or aromatic groups and wherein the polycarbonate contains one or more bisphenols; wherein the polycarbonate comprises an end-capping agent; wherein the polycarbonate comprises a branching agent; and wherein the polycarbonate containing the branching agent and the end-capping agent has a peak melt viscosity of greater than or equal to 7,000 poise when calculated from the equation of wherein the peak melt viscosity equals: $-57135.91+36961.39*BL+14001.13*MW^{1/3}-46944.24*pKa-322.51*BL*MW^{1/3}-2669.19*BL*pKa+215.83*MW^{1/3}*pKa+1125.63*BL^2-200.11*MW^{2/3}+2231.15*pKa^2$, wherein BL is the mole ratio of the branching agent in the formulation determined by dividing the number of moles of branching agent by the total number of moles of bisphenol or bisphenols in the composition, the MW is the weight-averaged molecular weight of the polycarbonate containing the branching agent and the end-capping agent as determined by gel permeation chromatography using polycarbonate standards, and the pKa is the pKa of the end capping agent; and wherein a molded article of the composition has a UL 94 V0 rating at a thickness of 2.0 mm, specifically at 1.5 mm, and more specifically at 1.0 mm.

In a further embodiment, the peak melt viscosity is greater than or equal to 25,000 as calculated by the above equation.

In another embodiment, a method of making an article of manufacture that has a V0 94 rating at a thickness 1.5 mm comprises: (a) providing a polycarbonate, wherein the polycarbonate has a repeating structural background of the following formula

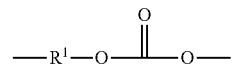

wherein greater than or equal to 60 percent of the total number of $R^1$ groups contain aromatic organic groups and the balance thereof are aliphatic, alicyclic, or aromatic groups and wherein the polycarbonate contains one or more bisphenols; an end capping agent that is not cyanophenol; a branching agent; (b) selecting the end-capping agent based upon the molecular weight of the polycarbonate and the branching level imparted by the branching agent, wherein the MVR of the polycarbonate is 1 to 15 $cm^3$/10 min and wherein the pKa of the end-capping agent is 8 to 11; (c) forming a polycarbonate containing the end-capping agent and the branching agent that has a peak melt viscosity that is greater than or equal to 7,000 poise when calculated from the equation of wherein the peak melt viscosity equals: $-57135.91+36961.39*BL+14001.13*MW^{1/3}-46944.24*pKa-322.51*BL*MW^{1/3}-2669.19*BL*pKa+215.83*MW^{1/3}*pKa+1125.63*BL^2-200.11*MW^{2/3}+2231.15*pKa^2$; and wherein BL is the mole ratio of the branching agent in the formulation determined by dividing the number of moles of branching agent by the total number of moles of bisphenol or bisphenols in the composition, the MW is the weight-averaged molecular weight of the formed polycarbonate as determined by gel permeation chromatography using polycarbonate standards, and the pKa is the pKa of the end capping agent; and (d) blending a flame retardant and a conversion material with the formed polycarbonate.

In a further embodiment, the peak melt viscosity is greater than or equal to 25,000 poise calculated from the above equation.

Branching Agents for Polycarbonate Containing Compositions

The polycarbonates herein may include branched polycarbonate(s). Various types of branching agents can be utilized for the embodiments encompassed by this disclosure.

Branched polycarbonate blocks can be prepared by adding a branching agent during polymerization. These branching agents include polyfunctional organic compounds containing at least three functional groups selected from hydroxyl, carboxyl, carboxylic anhydride, haloformyl, and mixtures of the foregoing functional groups. Specific examples include trimellitic acid, trimellitic anhydride, trimellitic trichloride (TMTC), tris-p-hydroxy phenyl ethane (THPE), 3,3-bis-(4-hydroxyphenyl)-oxindole (also known as isatin-bis-phenol), tris-phenol TC (1,3,5-tris((p-hydroxyphenyl)isopropyl)benzene), tris-phenol PA (4(4(1,1-bis(p-hydroxyphenyl)-ethyl) alpha, alpha-dimethyl benzyl)phenol), 4-chloroformyl phthalic anhydride, trimesic acid, and benzophenone tetracarboxylic acid. The branching agents can be added at a level of 0.05 to 2.0 wt %. Mixtures comprising linear polycarbonates and branched polycarbonates can be used.

In some embodiments, a particular type of branching agent is used to create branched polycarbonate materials. These branched polycarbonate materials have statistically more than two end groups. The branching agent is added in an amount (relative to the bisphenol monomer) that is sufficient to achieve the desired branching content, that is, more than two end groups. The molecular weight of the polymer may become very high upon addition of the branching agent and may lead to viscosity problems during phosgenation. Therefore, in some embodiments, an increase in the amount of the chain termination agent is used in the polymerization. The amount of chain termination agent used when the particular branching agent is used is generally higher than the instance when only a chain termination agent is used. The amount of chain termination agent used is generally above 5 mole percent and less than 20 mole percent compared to the bisphenol monomer.

In some embodiments, the branching agent is a structure derived from a triacid trichloride of the formula (19):

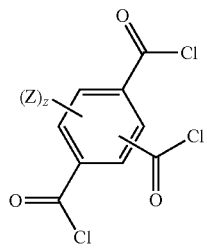

wherein, in this formula (19), Z is hydrogen, a halogen, $C_{1-3}$ alkyl group, $C_{1-3}$ alkoxy group, $C_{7-12}$ arylalkyl, alkylaryl, or nitro group, and z is 0 to 3; or a branching agent derived from a reaction with a tri-substituted phenol of the formula (20):

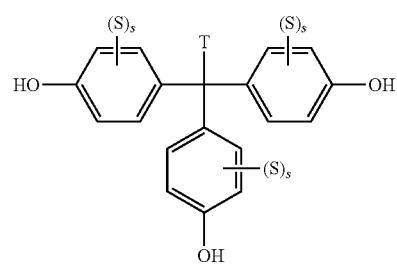

wherein, in this formula (20), T is a $C_{1-20}$ alkyl group, $C_{1-20}$ alkyleneoxy group, $C_{7-12}$ arylalkyl, or alkylaryl group, S is hydrogen, a halogen, $C_{1-3}$ alkyl group, $C_{1-3}$ alkoxy group, $C_{7-12}$ arylalkyl, alkylaryl, or nitro group, s is 0 to 4.

In another embodiment, the branching agent is a structure having formula (21):

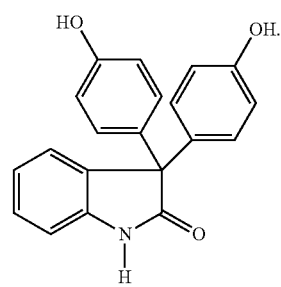

Examples of specific branching agents that are particularly effective in the compositions include trimellitic trichloride (TMTC), tris-p-hydroxy phenyl ethane (THPE) and isatin-bis-phenol. In one embodiment, in formula (19), Z is hydrogen and z is 3. In another embodiment, in formula (20), S is hydrogen, T is methyl, and s is 4.

The relative amount of branching agents used in the manufacture of the polymer will depend on a number of considerations, for example the type of $R^1$ groups, the amount of cyanophenol, and the desired molecular weight of the polycarbonate. In general, the amount of branching agent is effective to provide about 0.1 to 10 branching units per 100 $R^1$ units, specifically about 0.5 to 8 branching units per 100 $R^1$ units, and more specifically about 0.75 to 5 branching units per 100 $R^1$ units. For branching agents having formula (20), the amount of branching agent tri-ester groups are present in an amount of about 0.1 to 10 branching units per 100 $R^1$ units, specifically about 0.5 to 8 branching units per 100 $R^1$ units, and more specifically about 0.75 to 5 tri-ester units per 100 $R^1$ units. For branching agents having formula (21), the amount of branching agent tricarbonate groups are present in an amount of about 0.1 to 10 branching units per 100 $R^1$ units, specifically about 0.5 to 8 branching units per 100 $R^1$ units, and more specifically about 0.75 to 5 tri-phenylcarbonate units per 100 $R^1$ units. In some embodiments, a combination of two or more branching agents may be used.

In one embodiment, the polycarbonate of the composition has a branching level of greater than or equal to 1%, or greater than or equal to 2%, or greater than or equal to 3%, or 1% to 3%.

End-Capping Agents for Polycarbonate Containing Compositions

Various types of end-capping agents can be utilized herein provided that such agents do not significantly adversely affect the desired properties of the compositions, such as transparency, ductility, fire retardants, and the like.

Examples of endcapping agents (also referred to as chain stoppers) include certain mono-phenolic compound(s), and/or mono-carboxylic acid chloride(s), and/or mono-chloroformate(s). Mono-phenolic chain stoppers are exemplified by monocyclic phenols such as phenol and $C_1$-$C_{22}$ alkyl-substituted phenols such as p-cumyl-phenol, and p-t-butyl phenol; and monoethers of diphenols, such as p-methoxyphenol, phenols with phenols with cyano-substitution such as p-cyanophenol, or with halogen substitution such as p-flurophenol, or with nitro-substitution such as 4-nitrophenol. Alkyl-substituted phenols with branched chain alkyl substituents having 8 to 9 carbon atoms can be specifically mentioned. Certain mono-phenolic UV absorbers can also be used as an endcapping agent, for example 4-substituted-2-hydroxybenzophenones and their derivatives, aryl salicylates, monoesters of diphenols such as resorcinol monobenzoate, 2-(2-hydroxyaryl)-benzotriazoles and their derivatives, 2-(2-hydroxyaryl)-1,3,5-triazines and their derivatives, and the like. For example, the polycarbonate can have an end-cap comprising phenol, such as alkyl-substituted phenols, ether-substituted phenols, ester-substituted phenols, cyano-substituted phenols, and halogen substituted phenols, as well as combinations comprising at least one of the foregoing. Optionally, the end-capping agents can be selected from: cyanophenol and a phenol containing substitution(s) with aliphatic groups, olefinic groups, aromatic groups, halogens, ester groups, ether groups, and combinations comprising at least one of the foregoing.

Of particular usefulness commercially, the end-capping agents can be phenol, e.g., specifically, can be selected from: cyanophenol, para-t-butylphenol, para-cumylphenol, and combinations comprising at least one of the foregoing.

Additional thermoplastic material to which the method may be applied include polyethylene terephthalates (PET) and polybutylene terephthalate (PBT), polyethylene napthalate (PEN), polymethyl methacrylate (PMMA), polystyrene (PS), cyclic olefinic polymers (COP) and cyclic olefinic copolymers (COC), polyetherimide as well as polycarbonate/polyester blends.

The method is further illustrated by the following non-limiting examples.

EXAMPLES

Testing using the method according to the invention was conducted on four different transparent polycarbonate formulations. The polycarbonate samples for each formulation comprised square plates approximately 30×30 mm and 2.5 mm thick. Each sample transparent polycarbonate formulation was illuminated with light having a peak intensity centered on 459 nm (measured radiometrically) at an irradiance of 100,000 W/m² (calibration via an integrating sphere). The illumination of the samples was performed in an oven within which the air was maintained at a temperature of 120° C. Illumination was maintained over a series of 100 hour intervals for a total of 1,000 hours. At the end of each 100 hour interval the samples were allowed to cool and were visually inspected for their degree of discoloration. Samples which experienced catastrophic failure (i.e., melting, charring, burning) were removed from the oven between successive periods of illumination.

Test Sample 1 comprised a polycarbonate having the following formulation:

| | |
|---|---|
| Polycarbonate | 99.3-99.97 wt % |
| Mold Release Agent | 0.01-0.3 wt % |
| UV Absorber | 0.01-0.3 wt % |
| Stabilizer/Antioxidant | 0.01-0.1 wt % |
| Dyes | 1.39 ppm |

The polycarbonate plate of Test Sample 1 was first observed to yellow by 300 hours of illumination. Surface deformations in the sample were observed after 500 hours of illumination. By 600 hours of illumination catastrophic failure, in the form of a 1.5 cm diameter hole burned through the sample, was observed with charring and amber discoloration around the hole circumference. The test was halted for Test Sample 1 at 600 hours.

Test Sample 2 comprised a polycarbonate having the following formulation:

| | |
|---|---|
| Polycarbonate | 99.9-99.99 wt % |
| Mold Release Agent | — |
| UV Absorber | — |
| Stabilizer/Antioxidant | 0.01-0.1 wt % |
| Dyes | — |

The polycarbonate plate of Test Sample 2 survived the first 200 hours of illumination without significant discoloration. Catastrophic failure was observed at the 300 hour mark, at which point the test was halted.

Additional testing was also performed on two commercially available polycarbonate samples. Commercial Sample 1 survived 900 hours without significant discoloration. At 1000 hours the sample became hazy within the irradiance beam area and the test was halted. Commercial Sample 2 survived 1000 hours of illumination without significant discoloration.

What is claimed is:

1. A method for determining degradation of a thermoplastic, the method comprising:
   irradiating the thermoplastic with light having a peak intensity centered at a wavelength from 400 nm to 500 nm and an irradiance from 3,500 W/m² to 120,000 W/m² for a first period of time;
   maintaining ambient air surrounding the thermoplastic at a temperature from 23° C. to 175° C. during a second period of time;
   actively or passively cooling the thermoplastic;
   inspecting the thermoplastic for a first physical change in the thermoplastic after at least the first time period;

determining a rate of degradation based upon at least a comparison of the first physical change and a second physical change observed in the thermoplastic, repeating the irradiating, maintaining, inspecting, and determining steps for a plurality of successive time periods for a plurality of different thermoplastic formulations;

comparing the rate of degradation of the plurality of different thermoplastic formulation with one another; and selecting from among the different thermoplastic formulations, a formulation with the least degradation, wherein the plurality of successive time periods comprises up to 15 successive 100 hour time periods.

2. The method according to claim 1, wherein the first and second physical change comprises a discoloration of the thermoplastic.

3. The method according to claim 1, wherein inspecting the thermoplastic for a first physical change comprises measuring a degree of discoloration of the thermoplastic.

4. The method according to claim 3, wherein measuring the degree of discoloration of the thermoplastic comprises:
illuminating the thermoplastic with white light, a portion of the white light being transmitted through the thermoplastic; and
generating a transmission spectrum from the portion of the white light transmitted through the thermoplastic.

5. The method according to claim 3, wherein measuring the degree of discoloration of the thermoplastic comprises:
illuminating the thermoplastic with white light, a portion of the white light being reflected from the thermoplastic; and
generating a reflectance spectrum of the portion of the white light reflected from the thermoplastic.

6. The method of according to claim 3, further comprising comparing the degree of discoloration measured for the different thermoplastic formulations with one another.

7. The method according to claim 1, wherein the irradiance is from 70,000 W/m$^2$ to 110,000 W/m$^2$.

8. The method according to claim 1, wherein the irradiance is 100,000 W/m$^2$.

9. The method according to claim 1, wherein the peak intensity of the light is centered at a wavelength from 410 nm to 480 nm.

10. The method according to claim 1, wherein the peak intensity of the light is centered at a wavelength of 420 nm to 470 nm.

11. The method according to claim 1, wherein the peak intensity of the light is centered at a wavelength of 459 nm.

12. The method according to claim 1, wherein the peak intensity of the light is centered at a wavelength of about 450 nm.

13. The method according to claim 1, wherein the irradiance is about 50,000 W/m$^2$.

14. The method according to claim 1, wherein the ambient air is maintained at a temperature from 90° C. to 130° C.

15. The method according to claim 1, wherein the ambient air is maintained at a temperature of 120° C.

16. The method according to claim 1, wherein the thermoplastic is a polycarbonate.

17. The method according to claim 1, wherein inspecting the thermoplastic comprises a visual inspection for the physical change.

18. The method according to claim 1, wherein the method is used to evaluate thermoplastics for use in lighting appliances.

* * * * *